United States Patent [19]

Johnson et al.

[11] 4,247,715

[45] Jan. 27, 1981

[54] 2-ALKYNYL-5-INDANYLOXYACETIC ACIDS

[75] Inventors: Porter C. Johnson; William L. Matier, both of Evansville, Ind.

[73] Assignee: Mead Johnson & Company, Evansville, Ind.

[21] Appl. No.: 27,961

[22] Filed: Apr. 9, 1979

[51] Int. Cl.³ .............................................. C07C 59/90
[52] U.S. Cl. .............................. 562/462; 260/326.5 C; 260/326.8; 260/429.9; 260/439 R; 260/448 R; 260/448.8 R; 260/501.15; 260/501.16; 424/248.53; 424/250; 424/267; 424/274; 424/287; 424/289; 424/295; 424/316; 424/317; 544/107; 544/403; 546/206; 560/53
[58] Field of Search ................... 562/462; 260/501.15, 260/501.16, 448 R, 439 R, 326.5 B, 429.9, 326.8; 544/107, 403; 546/206

[56] References Cited

U.S. PATENT DOCUMENTS

| | | | |
|---|---|---|---|
| 3,974,212 | 8/1976 | Cragoe, Jr. et al. | 562/462 |
| 3,984,465 | 10/1976 | Cragoe, Jr. et al. | 562/462 |
| 4,070,539 | 1/1978 | Cragoe, Jr. et al. | 562/462 |
| 4,096,267 | 6/1978 | Cragoe, Jr. et al. | 562/462 |

OTHER PUBLICATIONS de Solms et al., J. Med. Chem., 21, 437–443 (1978).
Waltersdorf, Jr. et al., J. Med. Chem., 20, 1400–1408 (1977).

*Primary Examiner*—Vivian Garner
*Attorney, Agent, or Firm*—Robert H. Uloth; Robert E. Carnahan

[57] ABSTRACT

Indanyloxy compounds having 2-alkynyl substituents which exhibit diuretic, saluretic, and uricosuric activity are described. The compounds are obtained according to a process involving selective etherification of a 5-hydroxyindanone followed by alkynylation with a silylated alkynyl bromide to provide novel silylated intermediates which are hydrolyzed to indanyloxy compounds such as (6,7-dichloro-1-oxo-2-phenyl-2-propargyl-5-indanyloxy)acetic acid.

6 Claims, No Drawings

2-ALKYNYL-5-INDANYLOXYACETIC ACIDS

BACKGROUND OF THE INVENTION

1. Field of the Invention

This invention relates to novel indanyloxyacetic acid derivatives more specifically described as 1-oxo-2-(optionally substituted)phenyl-2-alkynyl-5-indanyloxyacetic acids. These compounds have drug and bio-affecting properties and, in particular, are diuretic and uricosuric agents with relatively low toxicity. The invention is also concerned with a method for preparing the indanyloxyacetic acid compounds and novel silylated intermediates therefor.

2. Description of the Prior Art

Cragoe, Jr., et al., U.S. Pat. No. 4,096,267 concerns (1-oxo-2-aryl-2-substituted-5-indanyloxy)alkanoic acids having diuretic, saluretic, and uricosuric activity. The following specific compounds of Formula (1) illustrate alkyl- and alkenyl-2-substituents.

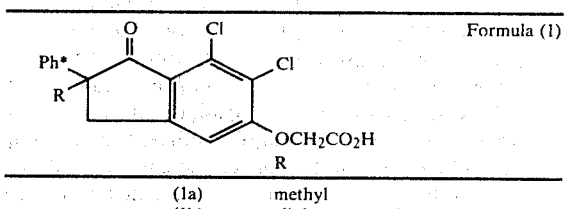

| | Formula (1) |
|---|---|
| (1a) | methyl |
| (1b) | allyl |

*Ph = phenyl

According to the U.S. Pat. No. 4,096,267, such compounds are prepared by various processes including an etherification step illustrated by the flow diagram below of the procedure of Example 1 (Step E).

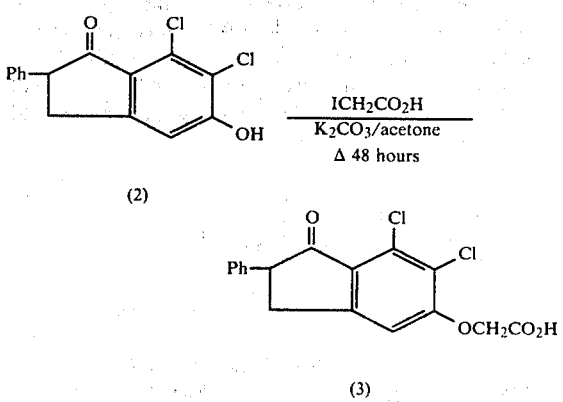

(1-Oxo-2-phenyl-6,7-dichloro-5-indanyloxy)acetic acid (3) is obtained according to the above flow diagram in a relatively low yield of about 6% with recovery of starting material even though an extended reaction period of some 48 hours was employed.

deSolms, et al., J. Med. Chem., 21, 437–443 (1978) discusses structure-activity relationships of the (2-alkyl-2-aryl-1-oxo-5-indanyloxy)acetic acids of U.S. Pat. No. 4,096,267. The article identifies the preferred compound of the series as (6,7-dichloro-2-methyl-1-oxo-2-phenyl-5-indanyloxy)acetic acid (MK-196). Using this compound as a standard for comparison, the authors concluded that as the "2-alkyl substituent" increases in size from methyl to ethyl, etc., activity drops considerably.

Cragoe, Jr., et al., U.S. Pat. No. 3,984,465 is concerned with (1-oxo-2-alkyl-2-substituted-5-indanyloxy)acetic acids having diuretic, saluretic, and uricosuric activity. Generically disclosed indanyloxyacetic acids include compounds wherein 2-substituents are alkyl, alkenyl, or alkynyl. The following compounds of formula (4) illustrating alkyl- and alkenyl-2-substituents are specifically disclosed in the U.S. Pat. No. 3,984,465. However, the patent does not describe or set forth in any manner a specific example of a "2-alkynyl" substituted indanyloxyacetic acid.

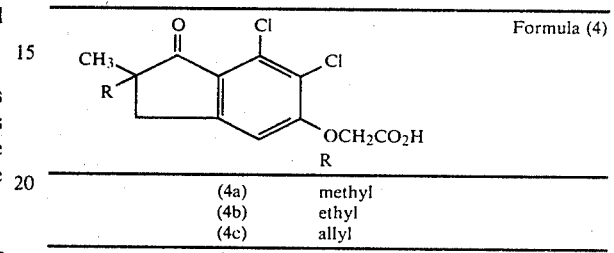

| | Formula (4) |
|---|---|
| (4a) | methyl |
| (4b) | ethyl |
| (4c) | allyl |

Cragoe, Jr., U.S. Pat. No. 4,070,539 concerns 2-alkyl derivatives of 1-oxo-5-indanyloxyalkanoic acid which are said to be diuretic and saluretic. Some of the compounds are reportedly also capable of maintaining or reducing uric acid levels.

Waltersdorf, Jr. et al., J. Med. Chem. 20, 1400–1408 (1977) discusses diuretic structure-activity relationships of certain (1-oxo-5-indanyloxy)acetic acids having a mono-alkyl substituent in the 2-position or bearing an additional "2-substituent" such as alkyl or allyl. The compounds studied were prepared according to processes described in Cragoe, et al., U.S. Pat. Nos. 3,984,465 and 4,070,539.

The instant invention provides a process for preparing indanyloxy compounds of Formula I (infra) involving selective etherification of a 2-(phenyl)-substituted-5-hydroxyindanone with ethyl bromoacetate to the corresponding indanyloxyacetate and subsequent alkynylation of the "2-position" with a "protected" alkynyl halide such as trimethylsilylpropargyl bromide followed by hydrolysis of the alkynyl intermediates. This process constitutes a decided improvement over analogous prior art procedures of Cragoe, et al., U.S. Pat. Nos. 4,070,539 and 4,096,267, in that substantially improved yields are obtained.

SUMMARY AND DETAILED DESCRIPTION OF THE INVENTION

Broadly described, this invention is concerned with novel indanyloxy compounds, and to a process and silylated intermediates for preparation thereof. The instant indanyloxy compounds possess diuretic and uricosuric properties which are valuable in treating conditions associated with electrolyte and fluid retention, particularly in the treatment of hypertension. The indanyloxy compounds of the instant invention are characterized by Formula I

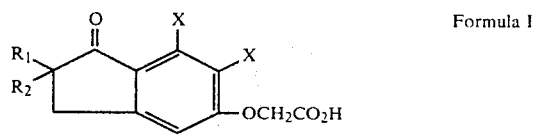

Formula I wherein
X is halo;
R₁ is phenyl or p-halophenyl;
R₂ is propargyl or 3-butynyl;
and a non-toxic pharmaceutically acceptable salt thereof.

It is to be understood that the term "halo" as used herein refers to bromine, iodine, and fluorine, and most preferably chlorine.

The term "non-toxic pharmaceutically acceptable salt" used herein refers to a combination of a Formula I compound with a relatively non-toxic base, the cation of which is relatively pharmaceutically ineffective in the usual dosage. Acceptable salts of the substances of Formula I include those of alkali metals, alkali earth metals and amines such as ammonia, primary and secondary amines, and quarternary ammonium hydroxides. Particularly preferred metal cations are those derived from alkali metals such as sodium, potassium, lithium, and the like; alkaline earth metals such as calcium, magnesium, and the like; and other metals such as aluminum, iron and zinc and other related metals. Preparation of the salts may be carried out in conventional manner by treating a solution or suspension of the acid with alkali metal and alkaline earth metal hydroxides, carbonates, bicarbonates, amines, or quarternary ammonium hydroxides to form the corresponding alkali metal, alkaline earth metal, amine or quaternary ammonium salts. Conventional concentration or crystallization techniques are employed in isolating the salts. Examples of primary, secondary or tertiary amines, or quaternary ammonium hydroxides providing pharmaceutically acceptable salts are: methylamine, dimethylamine, trimethylamine, ethylamine, N-methylhexylamine, benzylamine, alpha-phenylethylamine, ethylenediamine, piperidine, 1-methylpiperazine, morpholine, pyrrolidine, 1,4-dimethylpiperazine, ethanolamine, diethanolamine, triethanolamine, tetramethyl ammonium hydroxide, tetraethyl ammonium hydroxide, benzyltrimethyl ammonium, and the like.

The indanyloxy compounds characterized by Formula I are obtained by a series of reactions involving etherification of an appropriate 5-hydroxyindanone followed by alkynylation with a silylated alkynyl bromide to silylated intermediates which are hydrolyzed to the indanyloxy compounds of the invention as set forth in the following process steps which comprise (a) etherifying a 5-hydroxyindanone of Formula II

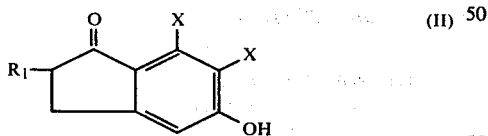

wherein R₁ is phenyl or p-halophenyl and X is halo with BrCH₂CO₂R₃ in which R₃ is lower alkyl of 1 to 4 carbon atoms inclusive in the presence of an alkali metal alkoxide in an alkanol solvent to provide an indanyloxyacetate of Formula III

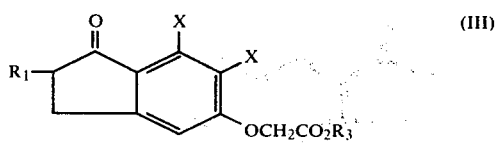

wherein X, R₁ and R₃ are as defined above;

(b) alkynylating the formula III compound with (CH₃)₃SiC≡C—(CH₂)ₙ—Br in which n is 1 or 2 in the presence of a carbonate base such as potassium or sodium carbonate in a reaction inert solvent such as dimethylformamide to provide a trimethylsilylalkynylindanyloxyacetic acid of Formula IV

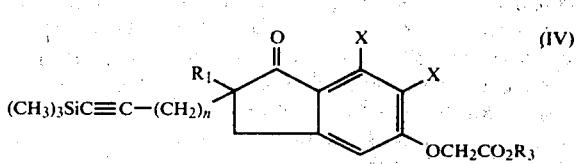

wherein X, n, R₁ and R₃ are as defined above;

(c) treating the formula IV compound with a concentrated solution (about 40–60%) of an alkali metal base such as sodium or potassium hydroxide in ethanol to provide the Formula I compound.

In the etherifying reaction (a) of the above process, selection of base and solvent is of particular importance with respect to preventing side reactions and maximizing yields of indanyloxyacetates of Formula III. Preferably, the reaction is carried out with an alkali metal alkoxide such as sodium or potassium alkoxide in an alkanol solvent such as methanol or ethanol. Bases such as sodium or potassium carbonate and solvents such as dimethylformamide or acetone are not suitable in that the reaction does not go to completion or substantial alkylation at the 2-position of the indanone starting material in addition to alkylation of the desired "5-OH" moiety results. For instance, reaction of 2-phenyl-5-hydroxy-6,7-dichloroindanone (IIa, R₁=phenyl, X=chloro) with ethyl bromoacetate in the presence of sodium ethoxide and ethanol provides indanyloxyacetate IIIa (R₁=phenyl, R₃=ethyl, X=chloro) in a 77% yield whereas reaction with ethyl bromoacetate in the presence of potassium carbonate employing dimethylformamide as solvent provided mixtures of IIIa and appreciable amounts of undesired 2-alkylated material of formula V.

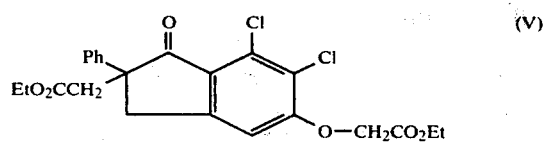

Table I below sets forth results of etherification attempts employing indanone IIa with various alkylating agents, bases and solvents.

TABLE 1

Etherification of 2-Phenyl-5-hydroxy-6,7-dichloroindanone (IIa)

| Alkylating Agent | Base | Solvent | Temperature/Time | Identified Material |
|---|---|---|---|---|
| ClCH₂CO₂Me | K₂CO₃ | acetone | reflux/4 hrs. | S.M.ᵃ |
| BrCH₂CO₂Et | K₂CO₃ | acetone | reflux/2.5 Hrs. | 1:1 mixture IIIa, V |
| BrCH₂CO₂Et | K₂CO₃ | DMF | 50°/1.5 hrs. | V and S.M. |
| BrCH₂CO₂Et | Cs₂CO₃ | acetone | reflux/5 hrs. | 1:1 mixture IIIa, V |
| BrCH₂CO₂Et | NaOEt | ethanol | reflux/5 hrs. | IIIa |

TABLE 1-continued

Etherification of 2-Phenyl-5-hydroxy-6,7-dichloroindanone (IIa)

| Alkylating Agent | Base | Solvent | Temperature/ Time | Identified Material |
|---|---|---|---|---|
| | | nol* | | |

*starting material.

Step (b) of the above process, wherein an alkynyl radical is attached to position 2 of the indanyloxyacetate (III), is preferably carried out with a silylated alkynyl halide such as 1-bromo-3-(trimethylsilyl)-2-propyne or 1-bromo-4-(trimethylsilyl)-3-butyne. The reaction may be conducted at temperatures ranging from about 25° to 80°, preferably at 55° to 65°, in the presence of a carbonate base such as potassium carbonate. Dimethylformamide is preferably employed as a reaction solvent but any solvent which is inert or substantially inert to the reactants and in which the reagents are reasonably soluble may be employed. The silylated intermediates of Formula III are obtained in nearly quantitative yield according to this procedure and can be generally used without further purification in step (c).

Step (c) of the above process (wherein the silylated indanone ester of Formula (IV) is converted to the corresponding Formula I product by base hydrolysis) is preferably carried out with a relatively concentrated solution of sodium hydroxide or potassium hydroxide in an alkanol solvent such as ethanol at 20°-30°. Preferably, from 3-12 (most preferably from 5-7) mole equivalents of a 50% solution of the base in ethanol is employed per each mole of silylated material. Selection of the solvent and base for the hydrolysis of the ester and desilylation is critical to maximizing yields of the Formula I compounds. For instance, treatment of methyl [1-oxo-2-phenyl-2-(3-trimethylsilylpropargyl)-6,7-dichloroindanyloxy]acetate at room temperature with 10% potassium hydroxide in methanol provides a 37% yield of Ia ($R_1$=phenyl, $R_2$=propargyl, X=chloro), m.p. 235°-241°. However, under these reaction conditions, ether interchange of the 5-(carbethoxymethoxy) function is also effected resulting in substantial production of the methyl ether of Formula VI, m.p. 161°-163°.

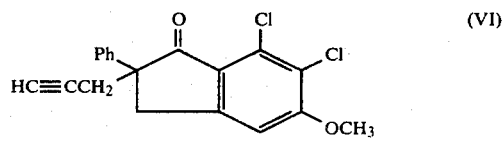

When the above hydrolysis and desilylation of step (c) is carried out with methyl or ethyl esters of [1-oxo-2-phenyl-2-(3-trimethylsilylpropargyl)-6,7-dichloroindanyloxy]acetic acid employing about 6 mole equivalents of 50% aqueous sodium hydroxide in ethanol, the yield of indanyloxy product Ia is substantially improved. For instance, the above mentioned ethyl ester in Step (c) afforded (6,7-dichloro-1-oxo-2-phenyl-2-propargyl-5-indanyloxy)acetic acid in 80-90% yield. Thus, the process of the instant invention as described in steps (a-c) above provides Formula I compounds from 5-hydroxyindanones of Formula II in overall yields of about 60-75%.

A preferred embodiment of the present invention is a process for preparing an indanyloxy compound characterized by Formula Ia

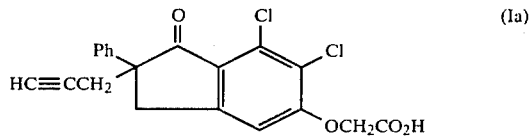

which comprises (a) etherifying a 5-hydroxyindanone of Formula IIa

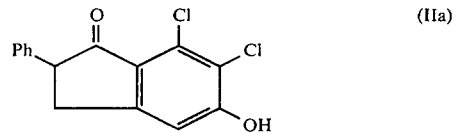

with ethyl bromoacetate in the presence of sodium ethoxide and absolute ethanol to provide an indanyloxyacetate of Formula IIIa

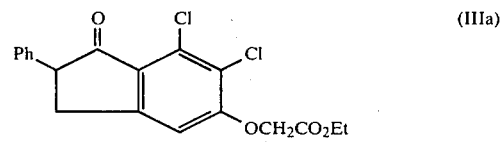

(b) alkynylating IIIa with 1-bromo-3-(trimethylsilyl)-2-propyne in the presence of potassium carbonate in dimethylformamide to provide a trimethylsilylalkynylindanyloxyacetic acid of Formula IVa

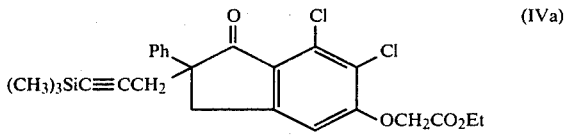

and thereafter;

(c) treating IVa with 50% sodium hydroxide or potassium hydroxide in ethanol to provide Ia.

As indicated hereinabove, the Formula I indanyloxy compounds are diuretic, saluretic, and uricosuric agents. When administered to mammals in conventional vehicles, these compounds effectively reduce the amount of sodium and chloride ions in the body and generally alleviate conditions usually associated with edema or fluid retention by reducing dangerous excesses of fluid levels with corresponding decrease in blood uric acid concentration.

For the purpose of treating excesses of fluid retention and associated diseases such as hypertension in mammals, the therapeutic process of the instant invention is carried out by systemically administering to a mammal in need of such treatment a diuretic, uricosuric or antihypertensive effective amount of a compound selected from the group characterized by Formula I or pharmaceutically acceptable salts thereof. By systemic administration, it is intended to include both oral and parenteral routes. Examples of parenteral administration are intramuscular, intravenous, intraperitoneal, rectal and subcutaneous administration. Dosage will vary with the form of administration and the particular compound chosen. However, from about 0.025 mg. to about 20 mg./kg. of body weight of a compound characterized by Formula I administered in effective single or multiple dosage units is generally satisfactory.

Indanyloxy Formula I compounds may be compounded and formulated with organic or inorganic solid materials or liquids which are pharmaceutically acceptable carriers to provide pharmaceutical compositions of unit dosage forms suitable for administration to mammals. The pharmaceutical compositions may take the form of tablets, capsules, powder, granules, suspension, solutions, and the like. Suitable pharmaceutical carriers comprise both solids and liquids such as corn starch, lactose, calcium phosphate, stearic acid, polyethyleneglycol, water, sesame seed oil, peanut oil, and so forth. Standard formulating procedures are employed to prepare the pharmaceutical compositions as illustrated by the following representative dosage form:

| Dry-Filled Capsules Containing 10 mg. of Active Ingredient Per Capsule | |
|---|---|
| Ingredient | Amount |
| (6,7-Dichloro-1-oxo-2-phenyl-2-propargyl-5-indanyloxy)acetic acid | 10 mg. |
| Lactose | 189 mg. |
| Magnesium stearate | 1 mg. |
| Capsule (Size No. 1) | 200 mg. |

The powdered (6,7-dichloro-1-oxo-2-phenyl-2-propargyl-5-indanyloxy)acetic acid, lactose and magnesium stearate are thoroughly admixed and then filled into No. 1 dry gelatin capsule.

The following examples further illustrate the present invention and will enable others skilled in the art to understand it more completely. It is to be understood that the invention is not limited solely to the particular examples given below. All temperatures expressed herein are in degrees Celsius. Regarding the "NMR" data given below, chemical shift delta values are in parts per million with tetramethylsilane as internal reference.

EXAMPLE 1

Preparation of (6,7-Dichloro-1-oxo-2-phenyl-2-propargyl-5-indanyloxy)acetic Acid STEP (a).- Sodium (629 mg., 27.3 mmol) is added to 50 ml. of absolute ethanol under a nitrogen atmosphere. After the sodium dissolves, 6,7-dichloro-5-hydroxy-2-phenyl-1-indanone (7.35 g., 25.1 mmol), and 75 ml. of additional absolute ethanol are added followed by 3.1 ml. of ethyl bromoacetate (28.1 mmol). The mixture is stirred at room temperature for 1 to 2 hrs., refluxed for 5–16 hrs. and then poured into a dilute acid-ether mixture. The crude reaction product collected and crystallized from 1:1 ethanol-water with activated charcoal provides a 70% yield of ethyl (6,7-dichloro-1-oxo-2-phenyl-5-indanyloxy)acetate, m.p. 113.5°–115°.

A sample of the indanyloxyacetate prepared according to the above procedure employing a 16 hr. reflux period and purified by ether trituration of the reaction product rather than crystallization melted at 113°–115° (77% yield) and had the following elemental analysis.

Anal. Calcd. for $C_{19}H_{16}Cl_2O_4$: C, 60.18; H, 4.26; Cl, 18.70. Found: C, 59.99; H, 4.36; Cl, 18.80.

NMR ($CDCl_3$): 1.31 (3,t, 7.5 Hz), 3.10 (1,dd, 4.2 and 16.2 Hz), 3.53 (1,dd, 7.5 and 16.2 Hz), 3.88 (1,dd, 4.2 and 7.5 Hz), 4.26 (2,q, 7.5 Hz), 4.80 (2,s), 6.76 (1,s), 7.22 (5,m).

STEP (b).- A solution of 1-bromo-3-(trimethylsilyl)-2-propyne (2.87 g., 15.0 mmol) prepared according to methods of Corey, Tet. Lett., 3963 (1973) and Miller, Syn. Comun., 2, 267 (1972) in 50 ml. of dimethylformamide is added to a mixture of ethyl (6,7-dichloro-1-oxo-2-phenyl-5-indanyloxy)acetate (2.9 g., 7.65 mmol) and powdered potassium carbonate (2.65 g., 19.2 mmol) under an argon atmosphere. After stirring at 60° for a period of 2 hr. and cooling to room temperature, ether is added to the reaction mixture followed by dilute hydrochloric acid. The acidified solution is extracted with ether and the ethereal extract sequentially washed with water and brine, and then dried over magnesium sulfate. Removal of solvent under reduced pressure affords 4.72 g. of tan solid. Crystallization of this material from cyclohexane provides 3.26 g., (87% yield) of ethyl [6,7-dichloro-1-oxo-2-phenyl-2-(3-(trimethylsilyl)-2-propynyl)-5-indanyloxy]acetate, m.p. 111.5°–113° (corr.).

Anal. Calcd. for $C_{25}H_{26}Cl_2O_4Si$: C, 61.35; H, 5.36. Found: C, 61.15; H, 5.29.

NMR ($CDCl_3$): -0.04 (9,s), 1.31 (3,t, 7.5 Hz), 2.94 (2,s), 2.58 (2,m), 4.30 (2,q, 7.5 Hz), 4.79 (2,s), 6.80 (1,s), 7.29 (5,m).

STEP (c).- A solution of 50% sodium hydroxide (2.5 g.) in 50 ml. of abs. ethanol is added to a suspension of ethyl [6,7-dichloro-1-oxo-2-phenyl-2-(3-(trimethylsilyl)-2-propynyl)-5-indanyloxy]acetate (3.08 g., 6.3 mmol) in 100 ml. of abs. ethanol under an argon atmosphere. The mixture stirred at room temperature for a period of 5 hr. (excluding light) and mixed with water provides a clear yellow solution which is first extracted with ether and then acidified with dilute hydrochloric acid. The acidified solution is extracted with 1:1 ether-ethyl acetate which, after washing with brine and drying over magnesium sulfate, is concentrated under reduced pressure to afford 2.22 g. (91% yield) of (6,7-dichloro-1-oxo-2-phenyl-2-propargyl-5-indanyloxy)acetic acid as a tan solid, m.p. 238.5°–241.5° (corr.). Crystallization from isopropanol affords the indanyloxyacetic acid product as white needles, m.p. 237.5°–240° (corr.). This material is solvated with 0.17 mole of isopropanol, according to NMR analysis, and has the following elemental analysis.

Anal. Calcd. for $C_{20}H_{14}Cl_2O_4 \cdot 0.17 C_3H_8O$: C, 61.68; H, 3.88. Cl, 17.76. Found: C, 61.46; H, 4.13; Cl, 17.55.

NMR (DMSO-$d_6$): 1.04 (1,d, 6.0 Hz), 2.74 (1,t, 2.0 Hz), 2.96 (2,d, 2.0 Hz), 3.55 (2,s), 5.01 (2,s), 7.28 (5,m), 7.38 (1,s), 13.20 (1,bs).

Analytically pure (6,7-dichloro-1-oxo-2-phenyl-2-propargyl-5-indanyloxy)acetic acid (m.p. 236°–240°)is also obtained by dissolving the isolated reaction product from the ether-ethyl acetate extract in dilute sodium hydroxide (employing activated charcoal) and reprecipitating with dilute hydrochloric acid.

Anal. Calcd. for $C_{20}H_{14}Cl_2O_4$: C, 61.72; H, 3.63; Cl, 18.22. Found: C, 61.33; H, 3.40; Cl, 18.20.

NMR (DMSO-$d_6$): 2.74 (1,m), 2.96 (2,m), 3.55 (2,s), 5.01 (2,s), 7.28 (5,m), 7.38 (1,s).

EXAMPLE 2

Preparation of Indanyloxyacetates of Formula III (1) Methyl (6,7-dichloro-1-oxo-2-phenyl-5-indanyloxy)-acetate.- Reaction of 6,7-dichloro-5-hydroxy-2-phenyl-1-indanone with methyl bromoacetate according to the procedure of Example 1, STEP (a), affords the title compound, m.p. 151.5°–153° (from benzenecyclohexane).

Anal. Calcd. for $C_{18}H_{14}Cl_2O_4$: C, 59.20; H, 3.87. Found: C, 59.30; H, 3.82.

NMR ($CDCl_3$): 3.33 (2,m), 3.83 (3,s), 3.90 (1,m), 4.81 (2,s), 6.79 (1,s), 7.22 (5,m).

(2) Ethyl [6,7-dichloro-1-oxo-2-(p-chlorophenyl)-5-indanyloxy]acetate.- Reaction of of 6,7-dichloro-5-hydroxy-2-(p-chlorophenyl)-1-indanone with ethyl bromoacetate according to the procedure of Example 1, STEP (a), affords the title compound, m.p. 159.5°-160° (crystallized from ethanol-acetone).

Anal. Calcd. for $C_{19}H_{15}Cl_3O_4$: C, 55.17; H, 3.66; Cl, 25.71. Found: C, 55.10; H, 3.60; Cl, 25.76.

NMR (CDCl$_3$): 1.32 (3,t, 7.2 Hz), 3.08 (1,dd, 4.5 and 17.6 Hz), 3.55 (1,dd, 8.2 and 17.6 Hz), 3.88 (1,dd, 4.5 and 8.2 Hz), 4.29 (2,q, 7.2 Hz), 4.80 (2,s), 6.78 (1,s), 7.16 (4,m). (3) Ethyl [6,7-dichloro-1-oxo-2-(p-fluorophenyl)-5-indanyloxy]acetate.- Reaction of 6,7-dichloro-5-hydroxy-2-(p-fluorophenyl)-1-indanone with ethyl bromoacetate according to the procedure of Example 1, STEP (a), affords the title compound. Crystallization from ethanol provides analytically pure material, m.p. 143°-144°.

Anal. Calcd. for $C_{19}H_{15}Cl_2FO_4$: C, 57.46; H, 3.81; Cl, 17.86. Found: C, 57.46; H, 3.80; Cl, 17.83.

NMR (CDCl$_3$): 1.31 (3,t, 7.2 Hz), 3.07 (1,dd, 4.0 and 17.4 Hz), 3.55 (1,dd, 8.0 and 17.4 Hz), 3.86 (1,dd, 4.0 and 8.0 Hz), 4.28 (2,q, 7.2 Hz), 4.80 (2,s), 6.79 (1,s), 7.04 (4,m).

(4) Ethyl [6,7-dibromo-1-oxo-2-phenyl-5-indanyloxy]acetate.- Reaction of 6,7-dibromo-5-hydroxy-2-phenyl-1-indanone with ethyl bromoacetate according to the procedure of Example 1, STEP (a), affords the title compound.

EXAMPLE 3

Preparation of Silated Indanone Esters of Formula IV (a) Methyl [6,7-dichloro-1-oxo-2-phenyl-2-(3-(trimethylsilyl)-2-propynyl)-5-indanyloxy]acetate.- Reaction of methyl (6,7-dichloro-1-oxo-2-phenyl-5-indanyloxy)acetate with 1-bromo-3-(trimethylsilyl)-2-propyne according to Example 1, STEP (b), affords the title compound, m.p. 125.5°-127° (from cyclohexane-methylene chloride) in 74% yield.

Anal. Calcd. for $C_{24}H_{24}Cl_2O_4Si$: C, 60.64; H, 5.09. Found: C, 60.36; H, 5.16.

NMR (CDCl$_3$): -0.04 (9,s), 2.95 (2,s), 3.46 (1,d, 18.0 Hz), 3.70 (1,d, 18.0 Hz), 3.84 (3,s), 4.83 (2,s), 6.80 (1,s), 7.30 (5,m).

(b) Ethyl [6,7-dichloro-1-oxo-2-(p-chlorophenyl)-2-(3-(trimethylsilyl)-2-propynyl)-5-indanyloxy]acetate. Reaction of ethyl [6,7-dichloro-1-oxo-2-(p-chlorophenyl)-5-indanyloxy]acetate with 1-bromo-3-(trimethylsilyl)-2-propyne according to the procedure of Example 1, STEP (b), affords the title compound, m.p. 103°-103.5°; purified by chromatography (silica-gel column eluted with chloroform-n-hexane) and crystallization from ether-cyclohexane.

Anal. Calcd. for $C_{25}H_{25}Cl_3O_4Si$: C, 57.32; H, 4.81; Cl, 20.31. Found: C, 57.24; H, 4.85; Cl, 20.47.

NMR (DMSO-d$_6$): -0.10 (9,s), 1.24 (3,5, 7.2 Hz), 2.94 (2,s), 3.47 (2,s), 4.20 (2,q, 7.2 Hz), 5.10 (2,s), 7.31 (5,m).

(c) Ethyl [6,7-dichloro-1-oxo-2-(p-fluorophenyl)-2-(3-(trimethylsilyl)-2-propynyl)-5-indanyloxy]acetate.- Reaction of ethyl [6,7-dichloro-1-oxo-2-(p-fluorophenyl)-5-indanyloxy]acetate with 1-bromo-3-(trimethylsilyl)-2-propyne according to the procedure of Example 1, STEP (b), affords the title compound as an oil.

NMR (CDCl$_3$): -0.10 (9,s), 1.22 (3,t, 7 Hz), 2.78 (2,s), 3.45 (2,m), 4.20 (2,q, 7 Hz), 4.72 (2,s), 6.73 (1,s), 7.2 (4,m).

(d) Ethyl [6,7-dibromo-1-oxo-2-phenyl-2(3-(trimethylsilyl)-2-propynyl)-5-indanyloxy]acetate.- Reaction of ethyl (6,7-dibromo-1-oxo-2-phenyl-5-indanyloxy)acetate with 1-bromo-3-(trimethylsilyl)-2-propyne according to the procedure of Example 1, STEP (b), affords the title compound.

(e) Ethyl [6,7-dichloro-1-oxo-2-phenyl-2-(4-(trimethylsilyl)-3-butyne)-5-indanyloxy]acetate.- Reaction of ethyl (6,7-dichloro-1-oxo-2-phenyl-5-indanyloxy)acetate with 1-bromo-4-trimethylsilyl)-3-butyne according to the procedure of Example 1, STEP (b), affords the title compound.

EXAMPLE 4

[6,7-Dichloro-1-oxo-2-(p-chlorophenyl)-2-propargyl-5-indanyloxy]acetic Acid.- Desilylation and hydrolysis of ethyl [6,7-dichloro-1-oxo-2-(p-chlorophenyl)-2-(3-(trimethylsilyl)-2-propynyl)-5-indanyloxy]acetate with sodium hydroxide in ethanol according to the procedure of Example 1, STEP (c), affords the title compound, m.p. 200°-201°.

Anal. Calcd. for $C_{20}H_{13}Cl_3O_4$: C, 56.70; H, 3.10; Cl, 25.11. Found: C, 56.37; H, 3.27; Cl, 25.16.

NMR (DMSO-d$_6$): 2.75 (1,t, 2.1 Hz), 2.96 (2,d, 2.1 Hz), 3.54 (2,s), 5.02 (2,s), 7.34 (5,m).

EXAMPLE 5

[6,7-Dichloro-1-oxo-2-(p-fluorophenyl)-5-indanyloxy]acetic Acid.- Desilylation and hydrolysis of ethyl [6,7-dichloro-1-oxo-2-(p-fluorophenyl)-2-(3-(trimethylsilyl)-2-propynyl)-5-indanyloxy]acetate with sodium hydroxide in ethanol according to the procedure of Example 1, STEP (c), affords the title compound, m.p. 189°-190°.

Anal. Calcd. for $C_{20}H_{13}Cl_2FO_4$: C, 58.99; H, 3.22; Cl, 17.42. Found: C, 58.92; H, 3.23; Cl, 17.69.

NMR (DSMO-d$_6$): 2.75 (1,t, 2.0 Hz), 2.95 (2,d, 2.0 Hz), 3.55 (2,s), 5.02 (2,s), 7.24 (5,m).

EXAMPLE 6

[6,7-Dichloro-1-oxo-2-phenyl-2-(3-butynyl)-5-indanyloxy]acetic Acid.- Desilylation and hydrolysis of ethyl [6,7-dichloro-1-oxo-2-phenyl-2-(4-(trimethylsilyl)-3-butyne)-5-indanyloxy]acetate with sodium hydroxide in ethanol according to the procedure of Example 1, STEP (c), affords the title compound.

EXAMPLE 7

(6,7-Dibromo-1-oxo-2-phenyl-2-propargyl-5-indanyloxy)acetic Acid.- Desilylation and hydrolysis of ethyl [6,7-dibromo-1-oxo-2-phenyl-2-(3(trimethylsilyl)-2-propynyl)-5-indanyloxy]acetate with sodium hydroxide in ethanol according to the procedure of Example 1, STEP (c), affords the title compound.

EXAMPLE 8

Preparation of 5-Hydroxyindanones of Formula II (a) 2,3-Dichloro-5-phenylacetylanisole.- Aluminum chloride (23.55 g., 176.6 mmol) is added portionwise to a stirred solution of 2,3-dichloroanisole (31.02 g., 175.2 mmol), phenylacetyl chloride (27.01 g., 174.7 mmol), and carbon disulfide (25 ml). with cooling at 0° over a 20 min. period. After standing at ambient temperature for 16 hrs., the carbon disulfide solvent is removed under reduced pressure. Residual material is slowly treated with a mixture of 50 ml. of concentrated hydrochloric acid and about 300 ml. of a water-ice mixture to give a light yellow solid which is taken up in methylene chloride. The methylene chloride solution washed with water, dried over magnesium sulfate, and concentrated under reduced pressure affords 84.7 g. of crude material which purified by crystallization from benzene-cyclohexane provides 38.7 g. (75% yield) of 2,3-dichloro-5-phenylacetylanisole, m.p. 127°–129.5°.

(b) 2,3-Dichloro-4-(2-phenylacryloyl)anisole.- Acetic anhyride (150 ml.) is added dropwise to a suspension of 2,3-dichloro-4-phenylacetylanisole (8.95 g., 30.3 mmol) in 15.3 ml. of N,N,N'N'-tetramethylenediaminomethane under an atmosphere of argon with icebath cooling. The reaction mixture stirred at 25° of 2 hrs. and poured into ice-water affords 11.9 g. of beige solid. An ethereal solution of the solid is washed with hydrochloric acid, water and then dried over magnesium sulfate. Removal of the solvent under reduced pressure provides 8.77 g. (94% yield) of 2,3-dichloro-4-(2-phenylacryloyl)anisole, m.p. 83.5°–86°.

(c) 2-Phenyl-5-methoxy-6,7-dichloro-1-indanone.- 2,3-Dichloro-4-(2-phenylacryloyl)anisole (8.2 g., 26.8 mmol) in 215 ml. of methylene chloride is added dropwise over a 4.5 hr. period to a stirred solution of 107 ml. of sulfuric acid in 107 ml. of methylene chloride at 0°–5° under an atmosphere of argon. Following addition, the reaction mixture is stirred for 0.5 hr., poured over about 300 g. of crushed ice and the aqueous-organic phases separated. The aqueous phase is extracted with methylene chloride and the combined methylene chloride solutions sequentially washed with water and then dried over magnesium sulfate. Removal of the solvent affords 8.52 g. of solid which crystallized from benzene-cyclohexane provides 4.59 g. (56% yield) of 2-phenyl-5-methoxy-6,7-dichloro-1-indanone, m.p. 193.5°–196.5°.

(d) 2-Phenyl-5-hydroxy-6,7-dichloro-1-indanone.- A stirred mixture of 2-phenyl-5-methoxy-6,7-dichloro-1-indanone (5.18 g., 16.8 mmol) and pyridine hydrochloride (23.3 g., 202 mmol) is heated at 190° for a period of 2 hrs. and then poured into 300 ml. of cold 2 N hydrochloric acid. Insolubles are collected, dried and crystallized from ethanol to afford 3.7 g. (75% yield) of 2-phenyl-5-hydroxy-6,7-dichloro-1-indanone, m.p. 252°–253.5°.

Following the above procedure of Example 8 (a-d) but employing an equimolar amount of the aralkyanoyl halides listed below:

p-chlorophenylacetylchloride,
p-fluorophenylacetylchloride, in place of phenylacetylchloride, there is produced, respectively, (1) 2-(p-chlorophenyl)-5-hydroxy-6,7-dichloro-1-indanone, m.p. 278°–280°. Anal. Calcd. for $C_{15}H_9Cl_3O_2$: C, 55.00; H, 2.77; Cl, 32.47. Found: C, 54.77; H, 2.81; Cl, 32.24.

(2) 2-(p-fluorophenyl)-5-hydroxy-6,7-dichloro-1-indanone, m.p. 275°–276°. Anal. Calcd. for $C_{15}H_9Cl_2FO_2$: C, 57.91; H, 2.92; Cl, 22.79. Found: C, 58.05; H, 2.71; Cl, 23.15.

Following the above procedure of Example 8 (a–d) employing 2,3-dibromoanisole for 2,3-dichloroanisole affords (3) 2-phenyl-5-hydroxy-6,7-dibromo-1-indanone.

What is claimed is:

1. An indanyloxy compound in Formula I

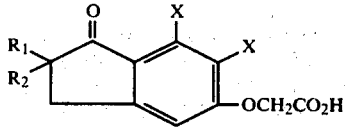

Formula I wherein
X is halo;
$R_1$ is phenyl or p-halophenyl;
$R_2$ is propargyl or 3-butynyl, and a pharmaceutically acceptable salt thereof.

2. The compound of claim 1 in which X is chloro.

3. The compound of claim 1 in which $R_1$ is phenyl and $R_2$ is propargyl.

4. The compound of claim 1 which is (6,7-dichloro-1-oxo-2-phenyl-2-propargyl-5-indanyloxy)acetic acid.

5. The compound of claim 1 which is [6,7-dichloro-1-oxo-2-(p-chlorphenyl)-2-propargyl-5-indanyloxy]acetic acid.

6. The compound of claim 1 which is [6,7-dichloro-1-oxo-2-(p-fluorophenyl)-2-propargyl-5-indanyloxy]acetic acid.

* * * * *